(12) United States Patent
Ding et al.

(10) Patent No.: US 10,345,197 B2
(45) Date of Patent: Jul. 9, 2019

(54) LOADING TEST TEST-AND-CONTROL SYSTEM AND METHOD OF VEHICLE LIFTER LIFTING UNIT

(71) Applicant: CRRC QINGDAO SIFANG ROLLING STOCK RESEARCH INSTITUTE CO., LTD., Qingdao (CN)

(72) Inventors: Hui Ding, Qingdao (CN); Jun Niu, Qingdao (CN); Xiaolei Zhao, Qingdao (CN); Cancan Zhang, Qingdao (CN); Xiaoming Cao, Qingdao (CN); Minghai Wang, Qingdao (CN); Zengchao Zhang, Qingdao (CN); Jinbiao Zhang, Qingdao (CN); Xu Wang, Qingdao (CN)

(73) Assignee: CRRC QINGDAO SIFANG ROLLING STOCK RESEARCH INSTITUTE CO., LTD., Shandong (CN)

(*) Notice: Subject to any disclaimer, the term of this patent is extended or adjusted under 35 U.S.C. 154(b) by 0 days.

(21) Appl. No.: 16/003,091

(22) Filed: Jun. 7, 2018

(65) Prior Publication Data

US 2018/0292297 A1 Oct. 11, 2018

Related U.S. Application Data

(63) Continuation of application No. PCT/CN2017/084357, filed on May 15, 2017.

(30) Foreign Application Priority Data

Mar. 30, 2017 (CN) .......................... 2017 1 0202439

(51) Int. Cl.
*G01M 1/00* (2006.01)
*G01N 3/02* (2006.01)
*G01M 99/00* (2011.01)

(52) U.S. Cl.
CPC ............ *G01M 99/007* (2013.01); *G01M 1/00* (2013.01); *G01M 99/00* (2013.01); *G01N 3/02* (2013.01)

(58) Field of Classification Search
CPC .................................................. G01M 99/007
See application file for complete search history.

(56) References Cited

U.S. PATENT DOCUMENTS 4,058,178 A * 11/1977 Shinohara ............. B66C 23/905
                                                          177/146
4,501,139 A *  2/1985 Petersen ................ G01M 17/06
                                                          73/115.01
(Continued)

FOREIGN PATENT DOCUMENTS

CN        1430053 A     7/2003
CN      102235943 A    11/2011
(Continued)

OTHER PUBLICATIONS

The International Search Report of corresponding International PCT Application No. PCT/CN2017/084357, dated Dec. 20, 2017.
(Continued)

*Primary Examiner* — Manuel L Barbee
*Assistant Examiner* — Raymond L Nimox
(74) *Attorney, Agent, or Firm* — J.C. Patents

(57) ABSTRACT

A loading test test-and-control system and method of vehicle lifter lifting unit, the system is used to test a lifting unit, comprising a base, the base is provided thereon with a support bracket capable of installing the lifting unit to be tested; the support bracket is provided with a loading unit for
(Continued)

applying a loading force to the lifting unit to be tested; the loading unit is electrically connected with a control unit which can control the pressure applied by the loading unit according to a set value. The method uses the system. Before the assembly of the vehicle lifter is completed, the system may carry out a loading test for the lifting unit and verify the function and static strength of the lifting unit, facilitating the test and saving cost.

19 Claims, 13 Drawing Sheets

(56) References Cited

U.S. PATENT DOCUMENTS

| | | | | |
|---|---|---|---|---|
| 5,230,392 | A * | 7/1993 | Tremblay | G01G 19/08 177/137 |
| 5,703,333 | A * | 12/1997 | Wegner | G01G 19/12 177/139 |
| 6,585,079 | B1 * | 7/2003 | Weyer | B66F 9/0655 182/18 |
| 6,912,916 | B1 * | 7/2005 | Joubert | B66C 15/00 73/856 |
| 8,708,107 | B2 * | 4/2014 | Finkbeiner | B66F 7/20 187/213 |
| 2004/0035224 | A1 * | 2/2004 | Kajiyama | B60N 2/002 73/862.474 |
| 2007/0199387 | A1 | 8/2007 | Asher | |
| 2016/0340156 | A1 * | 11/2016 | Ost | B66C 23/78 |
| 2018/0340818 | A1 * | 11/2018 | Oliver | G01G 19/18 |

FOREIGN PATENT DOCUMENTS

| | | |
|---|---|---|
| CN | 103424275 A | 12/2013 |
| CN | 104309636 A | 1/2015 |
| CN | 104568478 A | 4/2015 |
| CN | 105347233 A | 2/2016 |
| CN | 105716887 A | 6/2016 |
| CN | 106441968 A | 2/2017 |
| JP | S4920159 C | 2/1974 |
| JP | S5477188 A | 6/1979 |
| JP | S60117124 | 6/1985 |
| JP | 2000-118970 A | 4/2000 |
| JP | 2015-96825 A | 5/2015 |

OTHER PUBLICATIONS

Gao, Let, "Mine Rock Mechanic" Metallurgical Industry Press, (Jul. 31, 1979), pp. 27-28.

Nie, Jinfang, "Computer controlled multi-channel electro hydraulic servo loading system" The 8th Aircraft Control and Maneuvering Academic Exchange Meeting of the Chinese Aeronautical Society, (Dec. 8, 2001), pp. 265-269.

Wang, Meng et al., "Mobile Vehicle Lifting Jack Acceptance Test Method". Railway Quality Control, vol. 45, No. 2, (Feb. 28, 2017), pp. 18-21.

The extended European Search Report of corresponding European application No. 17836193.7-1001 / 3372979, dated Jan. 21, 2019.

The Chinese Search Report of corresponding Chinese application No. 201710202439.6, dated Aug. 22, 2018.

The Japanese Examination Report of corresponding Japanese application No. 2018-536721, dated Jan. 15, 2019.

* cited by examiner

LOADING TEST TEST-AND-CONTROL SYSTEM AND METHOD OF VEHICLE LIFTER LIFTING UNIT

CROSS-REFERENCE TO RELATED APPLICATION

This application is a continuation application of, and claims the priority benefit of International Application No. PCT/CN2017/084357, filed on May 15, 2017, which in turn claims the priority benefits of China patent application No. 201710202439.6, filed on Mar. 30, 2017. The contents of these prior applications are hereby incorporated by reference in their entirety.

TECHNICAL FIELD OF THE INVENTION

The present invention belongs to the field of test, in particular to the loading test test-and-control field of vehicle lifter lifting unit.

TECHNICAL BACKGROUND OF THE INVENTION

A vehicle lifter is a lifting apparatus for a maintenance vehicle currently used in the sections of a motor car and an urban rail car, and comprises a steel structure part, a lifting unit part (commonly, a vehicle body lifting unit, a bogie lifting unit, etc.) and an electric control part; wherein the vehicle body lifting unit comprises a middle support, a vertical support rod, a support head and a transmission part; the support head is vertically arranged at the top of the vertical support rod. The bogie lifting unit comprises a middle support, a bending arm support rod, a horizontal beam and a transmission part; the horizontal beam is arranged on the top of the bending arm support rod. The positions of the middle support and the transmission part are fixed, the vertical support rod and the bending arm support rod are provided by being parallel to a transmission screw and being perpendicular to the ground, and driving the screw via a motor, the positions of the vertical support rod and the bending support rod may be changed by being parallel to the screw. The vehicle lifter may be used for lifting an alignment car or an unassembled car, may replace all the bogies at the same time or replace one bogie, and may meet the requirements of disassembly, assembly and maintenance for vehicles.

Since the car is relatively expensive, in order to ensure the safe and reliable operation of the vehicle lifter device, the lifting unit thereof needs a loading test before leaving a factory, at present, there is no any device and method for the loading test of vehicle lifter lifting unit before leaving the factory at home and abroad.

SUMMARY OF THE INVENTION

In order to solve the above problems, the present application provides a loading test test-and-control system and method of vehicle lifter lifting unit, before the assembly of the vehicle lifter is completed, may carry out a loading test for the lifting unit and verify the function and static strength of the lifting unit, facilitating the test and saving cost.

To realize the above purpose, the present application adopts the following technical solution:

An embodiment of the present application provides a loading test test-and-control system of vehicle lifter lifting unit, might be used to test an assembled vehicle lifter lifting unit, comprising a base, the base is provided thereon with a support bracket capable of installing the lifting unit to be tested, the support bracket is provided with a loading unit for applying a loading force to the lifting unit to be tested, the loading unit is electrically connected with a control unit which may control the pressure applied by the loading unit according to a set value.

Another embodiment of the present application provides a loading test test-and-control system of vehicle lifter lifting unit, might be used to test the lifting unit, comprising a base, the base is provided thereon with a support bracket and the lifting unit to be tested; a loading unit is provided on the support bracket for applying a loading force to the lifting unit to be tested; the loading unit is electrically connected with a control unit that may control the pressure applied by the loading unit according to a set value. The lifting unit in the present application comprises a support head and a vertical support column.

As a preferred embodiment, the support bracket comprises a first support column and a second support column, both of which are provided on the base; a horizontal beam is provided between the first support column and the second support column; the lifting unit to be tested is positioned between the first support column and the second support column and positioned below the horizontal beam; the loading unit is mounted on the horizontal beam and positioned between the horizontal beam and the lifting unit to be tested. In particular, one end of the support head of the lifting unit is connected with the vertical support column, and the other end thereof is a cantilever end; the loading unit is positioned between the horizontal beam and the cantilever end.

As a preferred embodiment, the base may comprise a first platform and a second platform, the first platform is connected to the second platform via a second staircase; the second platform is above the first platform and close to the loading unit. Further, the lifting unit and the support bracket are mounted on the first platform.

As a preferred embodiment, a bottom of the base may be provided with a support structure, the support structure may be selected as a steel frame structure. A bottom of the support structure is connected to the first platform via a first staircase; the support structure is usually placed on the ground, in this way, an operator may walk through the staircases between the ground, the first platform and the second platform.

As a preferred embodiment, the loading unit comprises a hydraulic cylinder, a fixed end of the hydraulic cylinder is mounted on the support bracket, a piston end is close to the lifting unit to be tested, a bottom of the piston end of the hydraulic cylinder is provided with a pressure sensor capable of detecting loading pressure of the hydraulic cylinder, the pressure sensor is connected to the control unit to transmit a pressure signal sensed by the pressure sensor to the control unit.

As a preferred embodiment, the fixed end of the hydraulic cylinder is mounted below the horizontal beam, the piston end of the hydraulic cylinder and a joint provided at a lower end of the piston end are at a side close to the lifting unit to be tested; the pressure sensor is positioned below the joint, the joint and the pressure sensor are movably connected via a connecting member (s).

As a preferred embodiment, the connecting member is divided into a first connecting member and a second connecting member, both of which are preferably "L" shaped structures; an upper end of the first connecting member is fixed on the bottom of the piston end or on the joint, a lower end of the second connecting member is mounted on the pressure sensor; the first connecting member is provided with a first hole, and the second connecting member is provided thereon with a second hole matching the first hole; the first connecting member and the second connecting member are mounted together by providing a fixing member in the first hole and the second hole; wherein at least one of the first hole or the second hole is a vertically long hole. Two connecting members are preferably provided, and two connecting members are particularly preferably provided symmetrically with respect to the pressure sensor.

As a preferred embodiment, a lower end of the pressure sensor may also be provided with a sensor end cap. Preferably, the lower end of the second connecting member is fixed on the sensor end cap.

As a preferred embodiment, the bottom of the piston end or the lower end surface of the joint, the upper and the lower end surfaces of the pressure sensor, the upper and the lower end surfaces of the sensor end cap, and the contact surface of the lifting unit to be tested are provided as planes matching with each other. As a preferred embodiment, the control unit at least comprises a pressure collecting module capable of collecting the pressure signal, a pressure output module capable of outputting a pressure signal value, and a pressure control module capable of controlling the loading pressure of the hydraulic cylinder, which are electrically connected with the control unit.

As a preferred embodiment, the hydraulic cylinder is further equipped with a displacement sensor, the displacement sensor is used for detecting a displacement signal of the hydraulic cylinder. An upper end of the displacement sensor is mounted on the fixed end, and a lower end thereof is mounted on the bottom of the piston end or on the joint. In this case, the control unit at least comprises a displacement collecting module capable of collecting a displacement signal and a displacement output module capable of outputting a displacement signal value, which are electrically connected with the control unit.

As a preferred embodiment, the control unit is electrically connected with strain gauges attached to the lifting unit to be tested, the strain gauges is a three-dimensional strain rosette with 45° angle distribution, the control unit comprises a collecting module capable of collecting three-dimensional strain values of the strain rosette, a calculation module capable of calculating a main stress value of the lifting unit to be tested according to the strain values of the strain rosette, and a control module capable of outputting the main stress value in the calculation module, the collecting module is electrically connected to the calculation module, the calculation module is electrically connected to the control module.

As a preferred embodiment, the strain gauge is provided on the vertical support column of the lifting unit to be tested and close to a connection part of the vertical support column and the support head; three strain gauges form one strain rosette, the strain rosette comprises a first strain gauge provided horizontally, a second strain gauge provided vertically and a third strain gauge positioned between the horizontal direction and the vertical direction, being preferably at an angle of 45° to the previous two directions; wherein an x-axis where the first strain gauge is positioned is directed to the cantilever end of the support head, a y-axis where the second strain gauge is positioned is directed to the connecting direction of the support head and the vertical support column, a u-axis where the third strain gauge is positioned is positioned between the x-axis and the y-axis.

As a preferred embodiment, a plurality of the support brackets are provided side by side on the base, each support bracket is provided thereon with one independent loading unit, and each loading unit is electrically connected to the control unit.

Another embodiment of the present application provides a loading test test-and-control method of vehicle lifter lifting unit, which uses the above loading test test-and-control system of vehicle lifter lifting unit, comprises the following steps:

the control unit sends a control signal to the loading unit according to a rated pressure value;

the hydraulic cylinder of the loading unit receives the control signal and applies the rated pressure value as an initial pressure to the lifting unit to be tested; the hydraulic cylinder continuously increases the pressure value to a pressure value under multiplier of a preset rated pressure value during the process of pressure loading, the pressure sensor connected with the hydraulic cylinder feeds back in real-time the pressure signal, applied by the hydraulic cylinder, to the control unit to test the load pressure value;

the control unit simultaneously adjusts the applied pressure value according to a feedback pressure to control the loading pressure.

As a preferred embodiment, the method further comprises the following steps: when the hydraulic cylinder loads the pressure at the initial set pressure value, the displacement sensor senses an initial displacement value of the hydraulic cylinder and feeds back to the control unit; when the hydraulic cylinder applies the pressure to be the pressure value under multiplier of the preset rated pressure value, the displacement sensor senses a second displacement value of the hydraulic cylinder and feeds back to the control unit; the control unit calculates a difference value between the second displacement value and the initial displacement value and outputs the difference value as a test of a deflection value of the lifting unit to be tested.

As a preferred embodiment, the method further comprises the following steps: the control unit collects stress signals of the strain rosette attached on the lifting unit to be tested, the calculation module of the control unit calculates the main stress values according to the preset formulas to test the stress of the lifting unit to be tested.

As a preferred embodiment, in the step of testing the stress value, the preset formulas in the calculation module are as follows:

$$\varepsilon_{max} = \frac{1}{2}\left[(\varepsilon_x + \varepsilon_y) + \sqrt{2[(\varepsilon_x - \varepsilon_u)^2 + (\varepsilon_u - \varepsilon_y)^2]}\right], \quad (1)$$

$$\varepsilon_{min} = \frac{1}{2}\left[(\varepsilon_x + \varepsilon_y) = \sqrt{2[(\varepsilon_x - \varepsilon_u)^2 + (\varepsilon_u - \varepsilon_y)^2]}\right], \quad (2)$$

$$tg2\alpha_0 = \frac{2\varepsilon_u - \varepsilon_x - \varepsilon_y}{\varepsilon_x - \varepsilon_y}, \quad (3)$$

$$\sigma_1 = E \times (\varepsilon_{max} + \varepsilon_{min} \times v)/(1 - v^2), \quad (4)$$

$$\sigma_2 = E \times (\varepsilon_{min} + \varepsilon_{max} \times v)/(1 - v^2), \quad (5)$$

The calculation module sequentially calculates the stress values according to the above preset formulas; where, E is an elasticity modulus, $v$ is Poisson's ratio, $\varepsilon$ is the strain in each direction of the strain rosette, $\varepsilon_{max}$ is the calculated maximum strain, $\varepsilon_{min}$ is the calculated minimum strain, $\alpha_0$ is an angle between the maximum main stress and the x axis, $\sigma_1$ is the stress value consistent with $\varepsilon_{max}$ direction, $\sigma_2$ is the stress value consistent with $\varepsilon_{min}$ direction.

Compared with the prior art, the present application has the following advantages and positive effects:

1. The loading test test-and-control system of vehicle lifter lifting unit of the present application, by providing the support bracket capable of installing a vehicle body or a bogie, and installing the loading unit on the support bracket, can hence realize the test and control for the vehicle body or the bogie which is assembled individually, thus having convenient, simple and quick test.

2. The loading test test-and-control method of vehicle lifter lifting unit of the present application can perform a pressure test, a lifting deflection test and a stress test on the loading unit to be tested, thus reducing testing difficulty and testing cost and improves testing precision.

Figure 1:
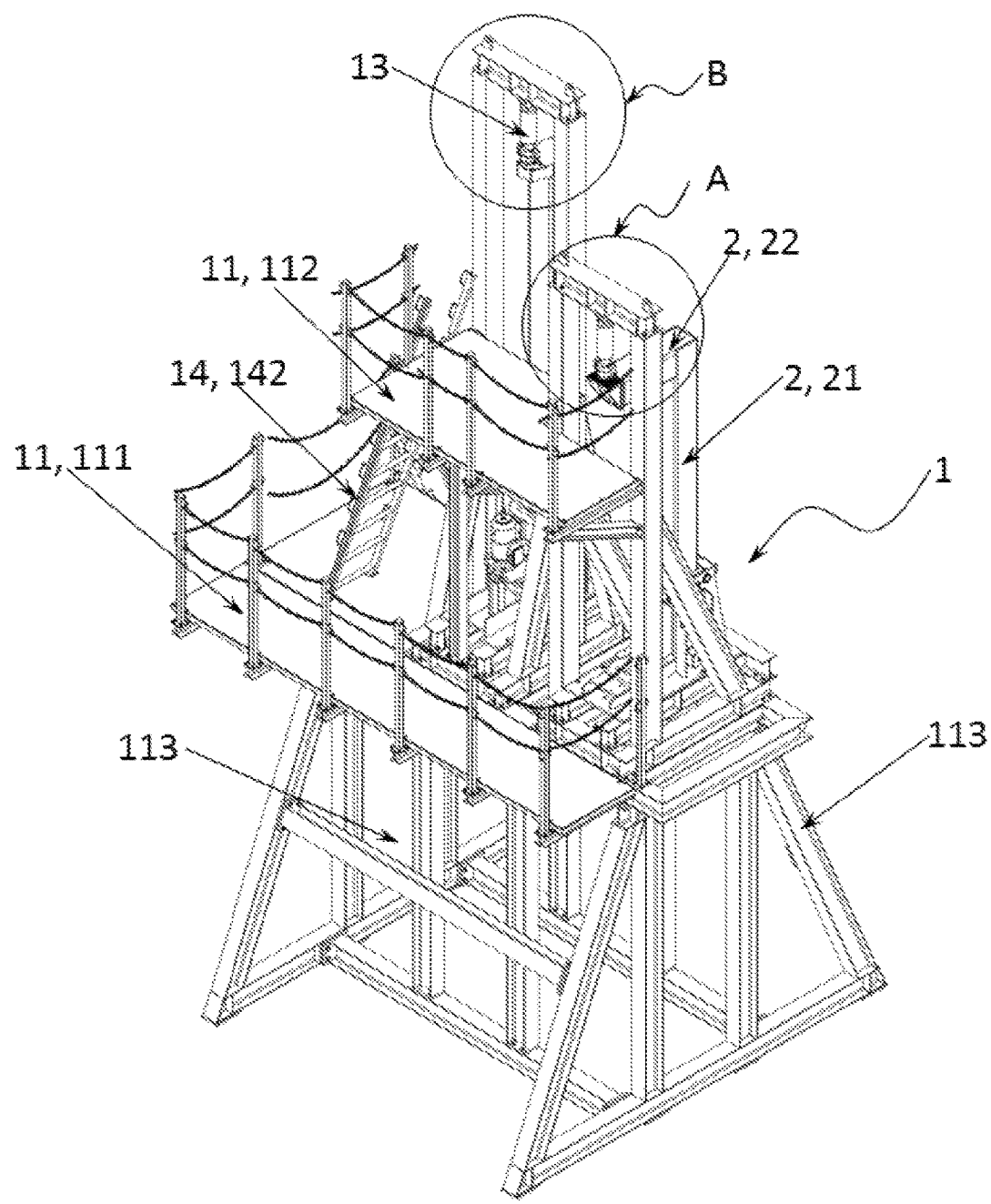
FIG. 1 is a front perspective view of a loading test test-and-control system.

1 Loading Test Test-and-Control System; 11 Base; 111 First Platform; 112 Second Platform; 113 Support Structure; 12 Support Bracket; 121 First Support Column; 122 Second Support Column; 123 Horizontal Beam; 13 Loading Unit; 131 Hydraulic Cylinder; 1311 Fixed End; 1312 Piston End; 1313 Joint; 132 Displacement Sensor; 1321 First Mounting Member; 1322 Second Mounting Member; 133 Pressure Sensor; 134 Sensor End Cap; 135 Connecting Member; 1351 First Connecting Member; 1352 Second Connecting Member; 136 First Hole; 137 Second Hole; 138 First Bolt; 139 Second Bolt; 140 Third Bolt; 14 Staircase; 141 First Staircase; 142 Second Staircase; 15 Strain Rosette;

2 Lifting Unit; 21 Vertical Support Column; 22 Support Head; 221 Cantilever End.

EMBODIMENTS OF THE INVENTION

In the following, the present application is specifically described by way of exemplary embodiments. However, it should be understood that elements, structures, and features of an embodiment may be beneficially incorporated into other embodiments without further recitation.

In the description of the present application, it should be noted that a height direction of the loading test test-and-control system of vehicle lifter lifting unit is a vertical direction after installation; the terms "up", "down", "front", "back" and the like indicate the positional or positional relationship according to the positional relationship shown in the drawings merely for the convenience of describing the present application and the simplified description, but do not indicate or imply a devices or an element referred to must be of a particular orientation, constructed and operated in a particular orientation and therefore should not be construed as limiting the present application.

Embodiment 1

Referring to FIGS. 1-7, a loading test test-and-control system 1 of vehicle lifter lifting unit of the present application may be used for testing the lifting unit 2 of a vehicle lifter, and comprise a base 11, the base 11 is provided thereon with a support bracket 12, the support bracket 12 is provided thereon with a loading unit 13 for applying a loading force to the lifting unit to be tested; the loading unit 13 is electrically connected with a control unit which may control the pressure applied by the loading unit 13 according to a set value, since an electric connection relationship is provided between the loading unit 13 and the control unit, the control unit is not shown in the drawings because the electric connection relationship may be understood according to common knowledge.

The vehicle lifter comprises the lifting unit 2, the lifting unit 2 may be directly mounted on the base 11 and also be mounted on the support bracket 12, when the latter is selected, since the support bracket 12 is provided on the base 11, the lifting unit 2 may be simultaneously fixed on the base 11 via a fixing seat of the support bracket 12. Two lifting units 2 are shown in FIG. 1, each lifting unit 2 comprises a vertical support column 21 and a support head 22, the support head 22 is provided horizontally, one end of the support head connected to the vertical support column 21 and the other end thereof is a cantilever end 221, and the structure of the lifting unit 2 may be considered as prior art or common knowledge; the lifting unit 2 on the right in FIG. 1 (i.e. the lifting unit in part A) is the lifting unit of a bogie, and the lifting unit 2 on the left (i.e. the lifting unit in part B) is the lifting unit of a vehicle body; However, the lifting unit that may be tested in the present invention is not limited to these two types, and is not limited to a test-and-control system provided with only two lifting units, one or more lifting units may be provided according to actual needs.

As shown in FIGS. 1-6, the base 11 may comprise a first platform 111 and a second platform 112, the first platform 111 may be connected to the second platform 112 via a second staircase 142; the second platform 112 is positioned above the first platform 111 and near the loading unit 13; in this manner, the loading unit 13 may be maintained on the second platform 112 or components of the loading unit 13 may be provided. The lifting unit 2 and the support bracket 12 are mounted on the first platform 111.

The bottom of the base 11 may be provided with a support structure 113, and the support structure 113 may select a steel frame structure so as to support the entire loading test test-and-control system 1 safely and stably. The bottom of the support structure 113 may be connected to the first platform 111 via a first staircase 141; the support structure 113 is generally placed on the ground, in this manner, an operator may walk between the ground, the first platform 111 and the second platform 112 through the staircases 14.

Figure 2:
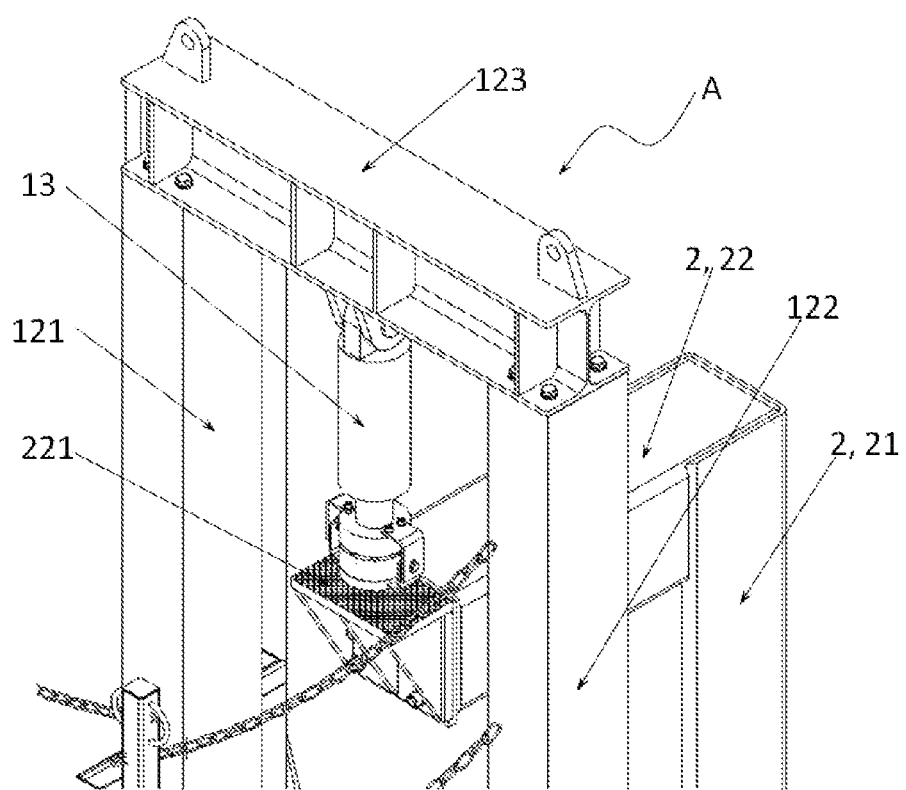
FIG. 2 is an enlarged view of part A in FIG. 1.
Figure 3:
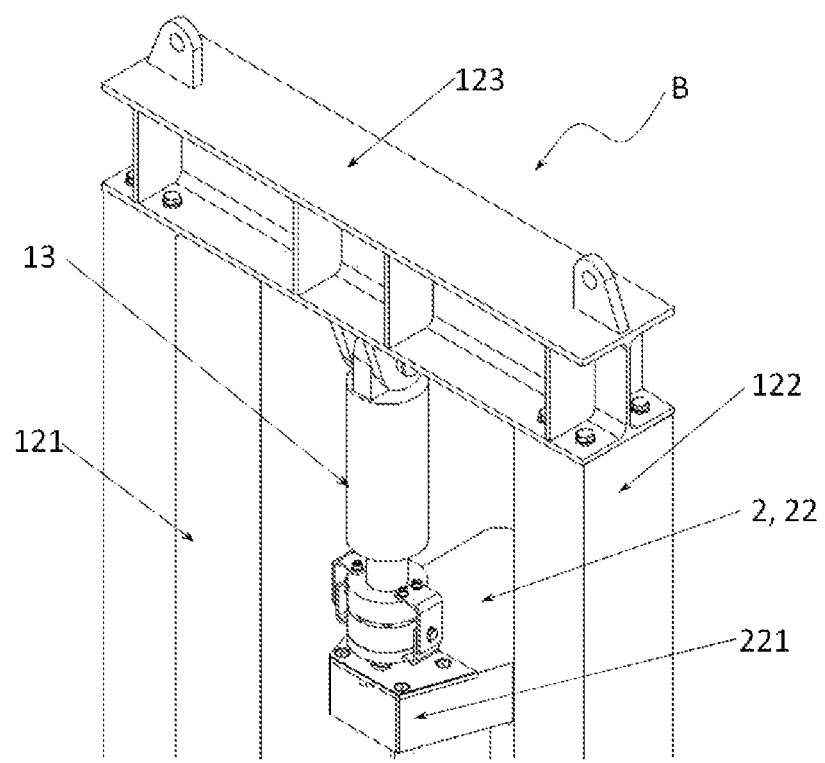
FIG. 3 is an enlarged view of part B of FIG. 1.
Figure 4:
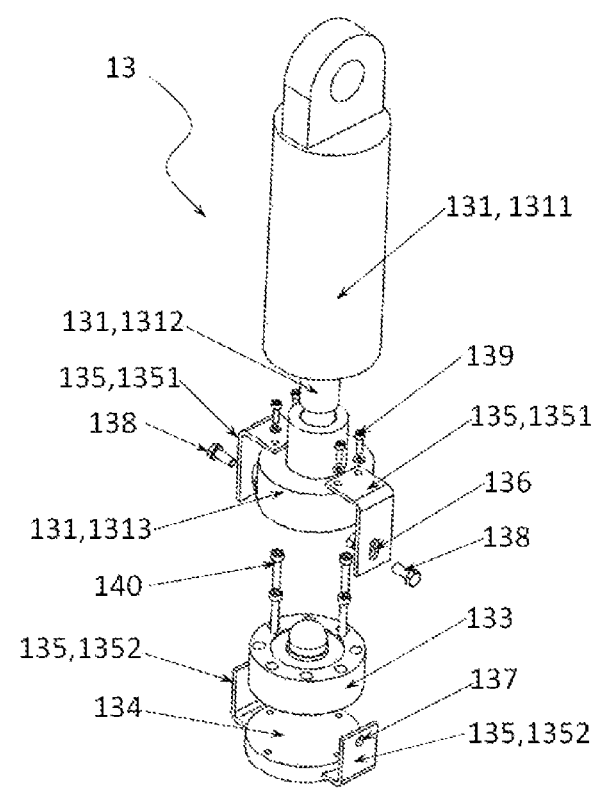
FIG. 4 is a top exploded perspective view of a loading unit.
Figure 5:
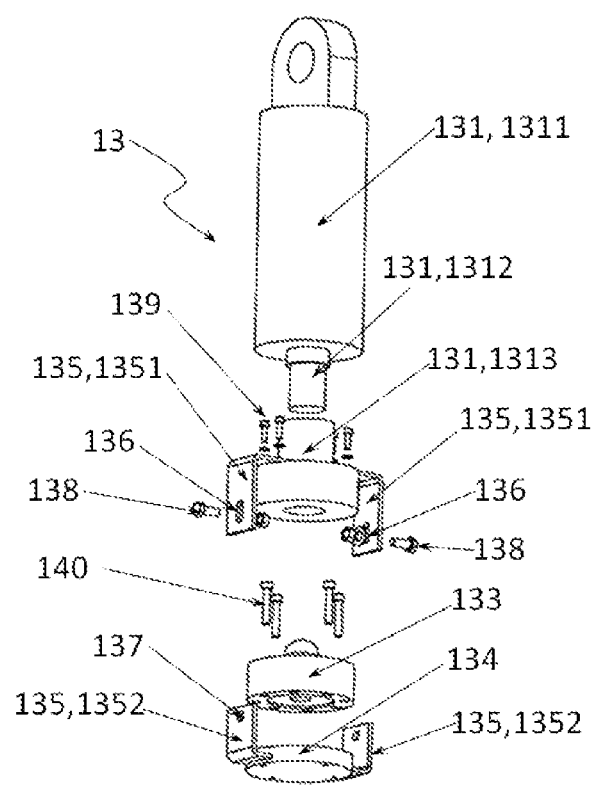
FIG. 5 is a bottom exploded perspective view of a loading unit.
Figure 6:
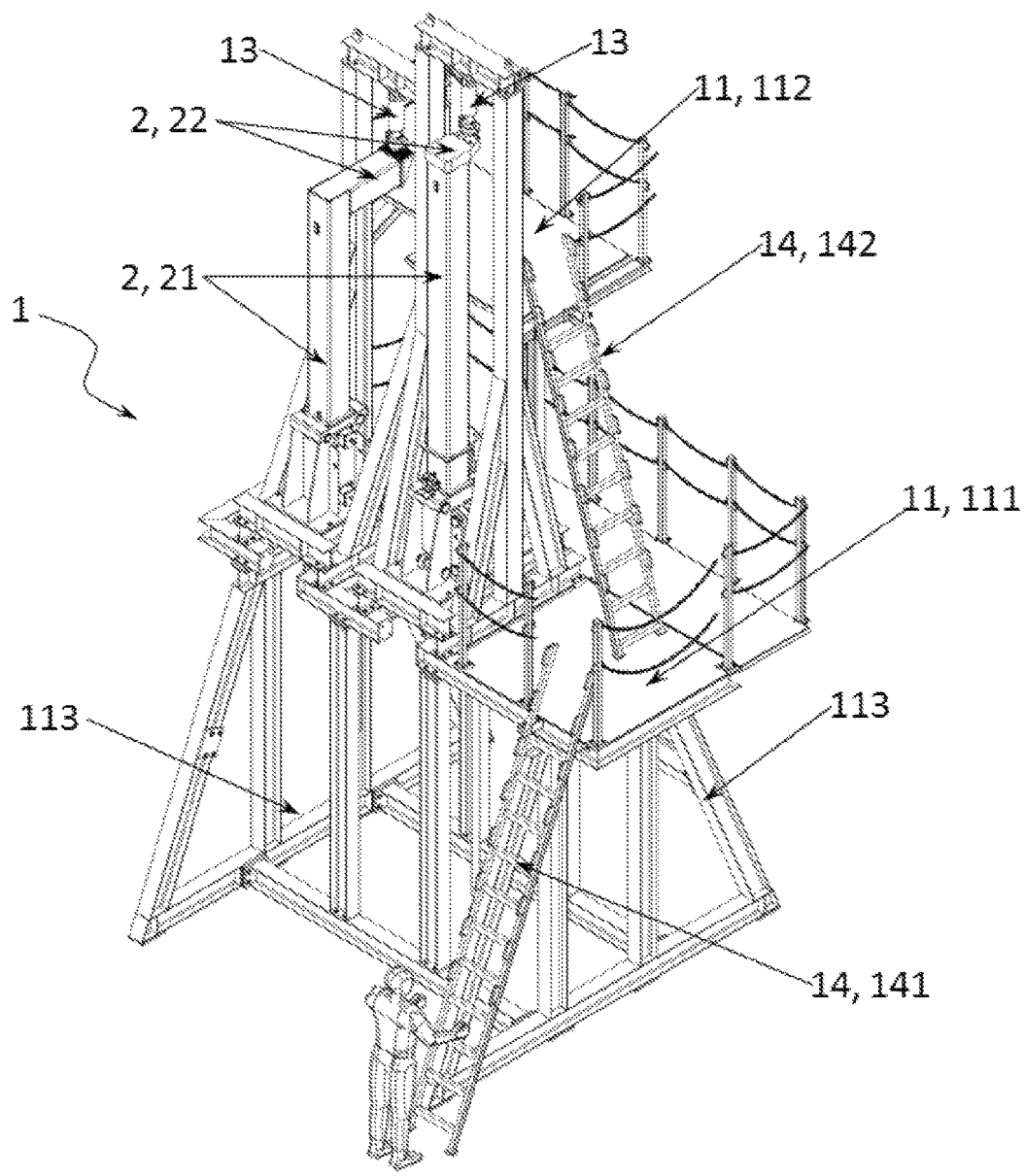
FIG. 6 is a rear perspective view of the test-and-control system.
Figure 7:
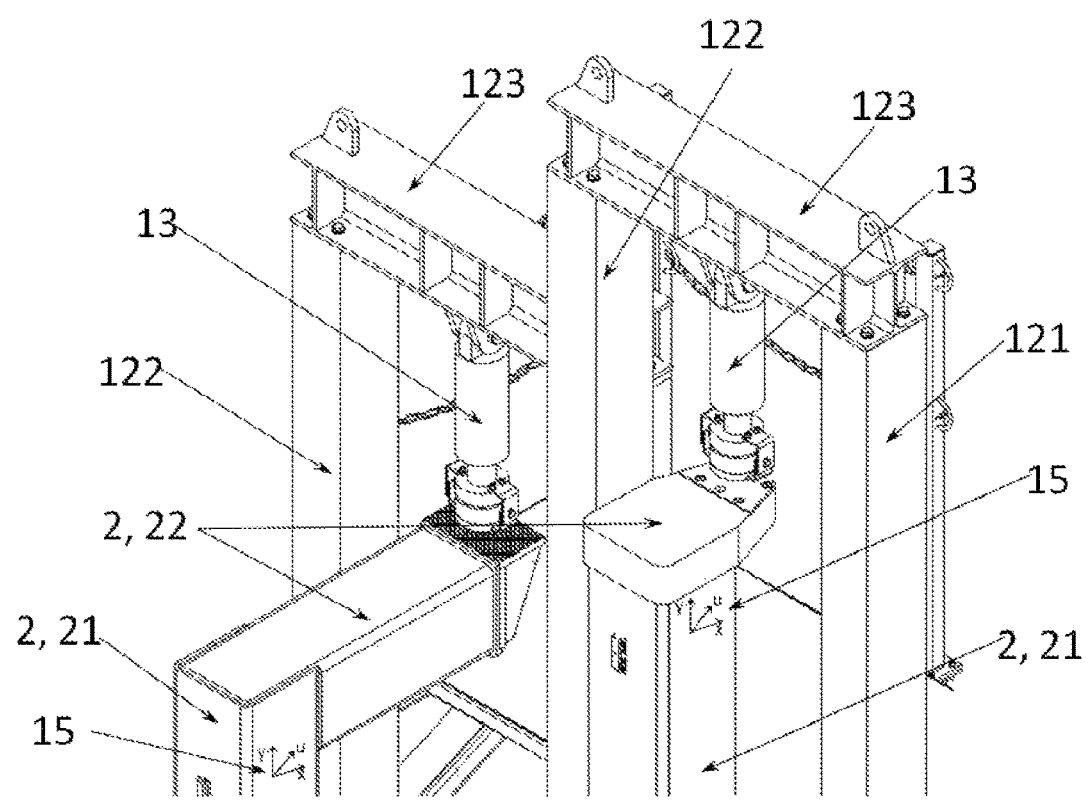
FIG. 7 is a partial enlarged view of FIG. 6.
Figure 8:
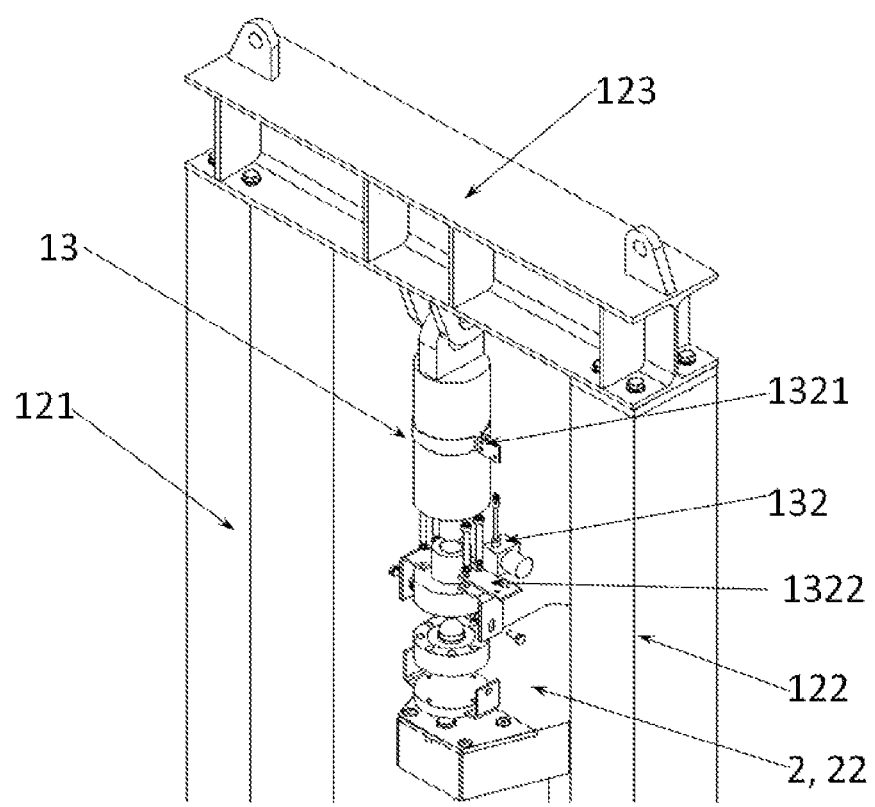
FIG. 8 is a partial front exploded perspective view of Embodiment 2.
Figure 9:
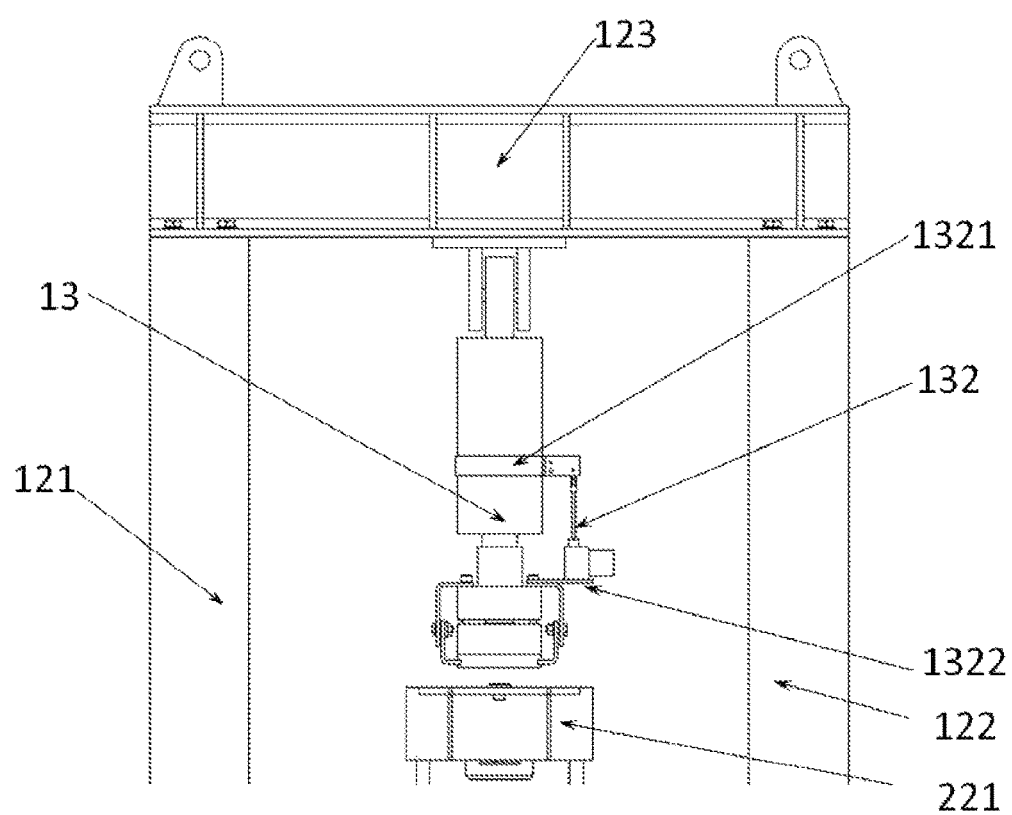
FIG. 9 is a partial front view of Embodiment 2.
Figure 10:
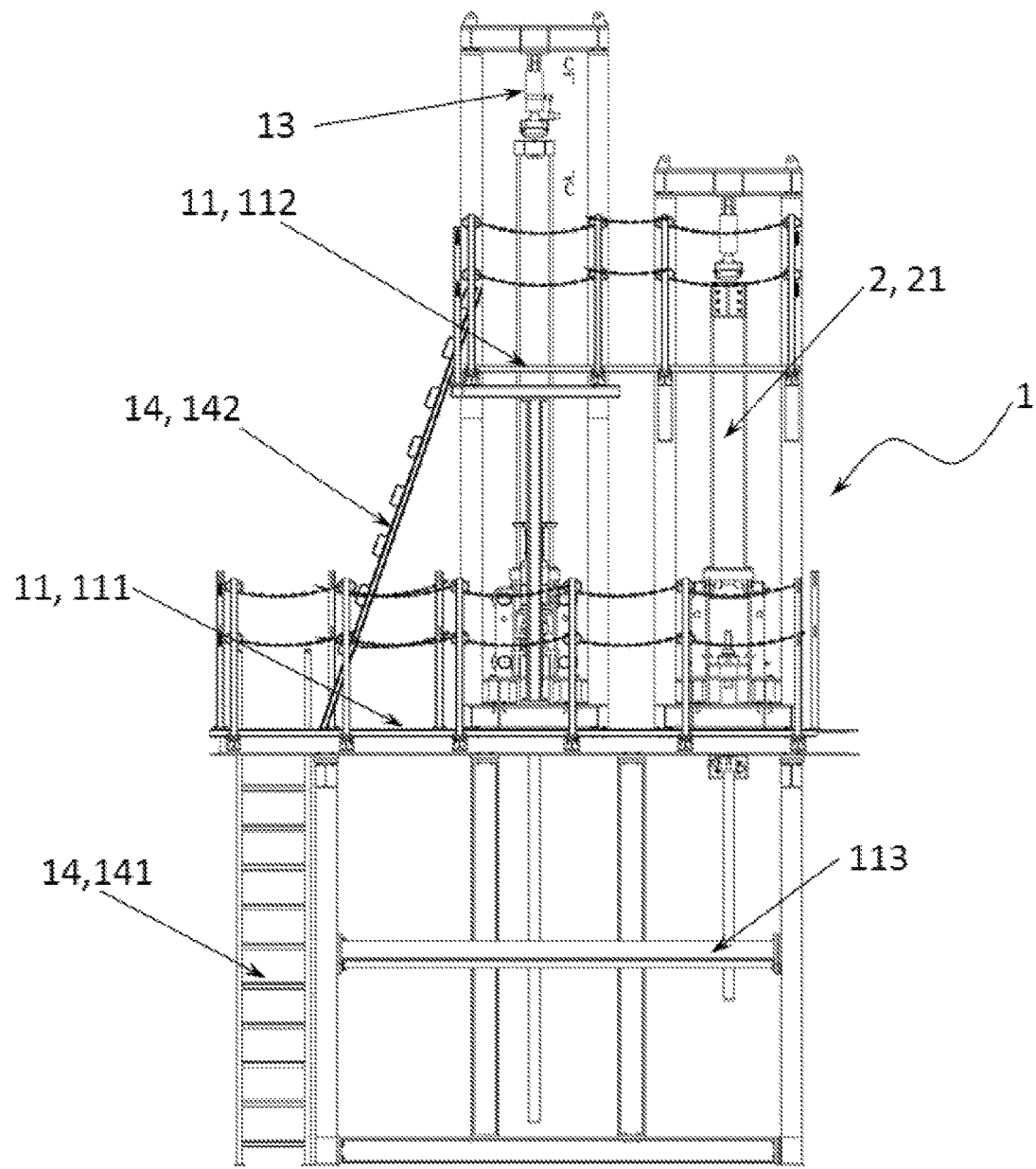
FIG. 10 is a front view of Embodiment 2.

The support bracket 12 may comprise a first support column 121 and a second support column 122, a horizontal beam 123 is provided between the first support column 121 and the second support column 122. The lifting unit 2 to be tested is mounted on the base 11 or the support bracket 12, and the support head 22 of the lifting unit 2 is positioned between the first support column 121 and the second support column 122 and positioned under the horizontal beam 123; the loading unit 13 is mounted at a bottom end of the horizontal beam 123 and positioned between the horizontal beam 123 and the support head 22; specifically, the loading unit 13 is positioned between the horizontal beam 123 and the cantilever end 221 of the support head 22 (as shown in FIGS. 2, 3, and 7).

Combined with FIG. 2-5, the loading unit 13 comprises a hydraulic cylinder 131, a fixed end 1311 of the hydraulic cylinder 131 (i.e. a cylinder barrel end of the hydraulic cylinder) is mounted on the support bracket 12, a piston end is close to the lifting unit 2 to be tested, a bottom of the piston end of the hydraulic cylinder 131 is provided with a pressure sensor 133 capable of detecting the loading pressure of the hydraulic cylinder. The pressure sensor 133 is connected to the control unit to transmit a pressure signal sensed by the pressure sensor 133 to the control unit.

Specifically, the loading unit 13 comprises the hydraulic cylinder 131, the fixed end 1311 of the hydraulic cylinder 131 is mounted under the horizontal beam 123, a lower end of the piston end 1312 may also be provided with a joint 1313, the joint 1313 may be of a flat cylinder shape so that the joint may be used for distributing the pressure from the hydraulic cylinder 131 evenly, therefore, an upper end of the joint 1313 may be fixedly connected to a bottom part of the piston end;

A pressure sensor 133 is provided under the joint 1313, a lower end of the pressure sensor 133 may be also provided with a sensor end cap 134, for example, a third bolt 140 may be used for fixing the pressure sensor 133 to the sensor end cap 134; the sensor end cap 134 is in contact with the lifting unit 2 to be tested, which may protect the pressure sensor 133 and reduce abrasion caused by the pressure sensor 133 directly contacting the lifting unit 2 to be tested; at the same time, the sensor end cap 134 is configured to match the shape of the lifting unit 2 to be tested, so as to facilitate the transmission of a force;

The loading unit 13 further comprises connecting members 135, therein, two connecting members 135 may be provided, and preferably provided symmetrically with respect to the pressure sensor 133; each connecting member 135 is divided into a first connecting member 1351 and a second connecting member 1352, both of which may be selected as "L" shaped steel plates; wherein an upper end of the first connecting member 1351 is fixed on the joint 1313, for example, second bolts 139 are used for fixation; when the joint 1313 is not provided, it may be fixed on the piston end; a lower end of the second connecting member 1352 is fixed on the sensor end cap 134; when the sensor end cap 134 is not provided, the second connecting member 1352 may also be mounted on the pressure sensor 133; the first connecting member 1351 is provided with a first hole 136, and the second connecting member 1352 is provided with a second hole 137 matching with the first hole 136; a fixing member, such as a first bolt 138, is provided in the second hole 137 and the first hole 136, so that the first connecting member 1351 and the second connecting member 1352 are mounted together; wherein, at least one of the first hole 136 and the second hole 137 is a vertical long hole, therefore, when no pressure is applied, the pressure sensor 133 automatically drops and does not come in contact with the joint 1313; when pressure is applied, the fixing member (the first bolt 138) moves along the long hole, and thus the joint 1313 and the pressure sensor 133 are fitted and transmit pressure; as shown in FIG. 2-5, the first hole 136 is the vertical long hole, so that the length of the connected connecting member 135 is adjustable in the vertical direction.

In addition, in order that the pressure sensor 133 can feel the pressure more sensitively, the lower end surface of the bottom of the piston end or the joint 1313, the upper and lower end surfaces of the pressure sensor 133, the upper and lower end surfaces of the sensor end cap 134 and the contact surface of the lifting unit 2 to be tested are provided as planes matching each other, in this way, the load pressure of the hydraulic cylinder 131 may be more directly transmitted to the lifting unit 2 to be tested.

Because the pressure sensor 133 is electrically connected with the control unit (not shown in the drawings), the pressure sensor 133 transmits the sensed pressure signal to the control unit, the control unit detects the pressure signal, at the same time, the control unit further controls the loading pressure of the hydraulic cylinder 131 according to a pressure value transmitted by the pressure signal, so as to realize the pressure detection and the loading test of the control unit on the lifting unit to be tested. In summary, the control unit at least comprises a pressure collecting module capable of collecting the pressure signal, a pressure output module capable of outputting a pressure signal value, and a pressure control module capable of controlling the pressure applied by the hydraulic cylinder 131, which are all electrically connected with the control unit.

Embodiment 2

Based on Embodiment 1, referring to FIGS. 8-11, the hydraulic cylinder 131 is further provided with a displacement sensor 132, an upper end of the displacement sensor 132 is provided on the fixed end 1311, and a lower end thereof is provided on the joint 1313 (at the piston end when no joint is available); for example, a first mounting member 1321 surrounding the fixed end may be provided on the fixed end 1311 for fixing the upper end of the displacement sensor 132; a second mounting member 1322 may be provided on the joint 1313 for fixing the lower end of the displacement sensor 132; the second mounting member 1322 may be a steel plate and is fixed on the joint 1313 via bolts, screws or the like.

Since the displacement sensor 132 is used for detecting the displacement signal of the hydraulic cylinder 131, the displacement sensor 132 herein is preferably a pull rope displacement sensor; the displacement sensor 132 is electrically connected to the control unit to transmit the displacement signal sensed by the displacement sensor 132 to the control unit. In summary, the control unit at least comprises a displacement collecting module capable of collecting the displacement signal and a displacement output module capable of outputting a displacement signal value, and the above modules are all electrically connected to the control unit.

Embodiment 3

Figure 11:
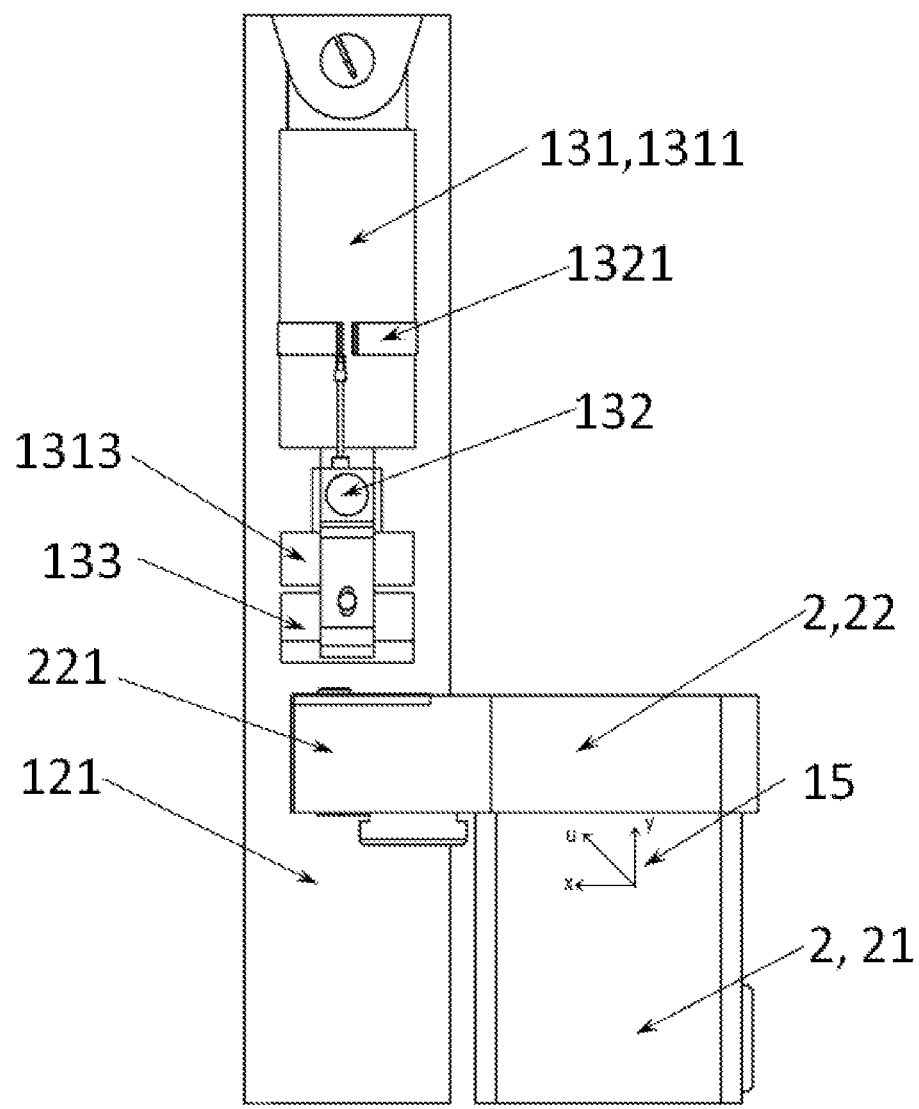
FIG. 11 is a C-C view of FIG. 10.
Figure 12:
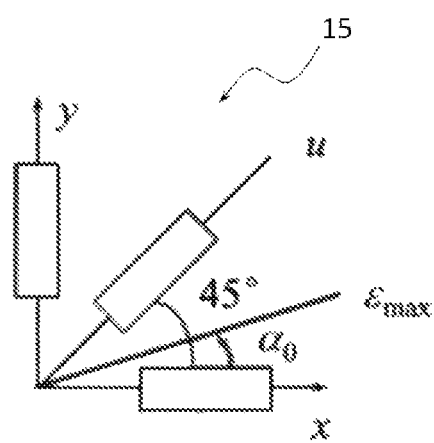
FIG. 12 is an orientation schematic view of a strain gauge.

Based on Embodiment 1 or 2, the control unit is electrically connected with a strain gauge attached to the lifting unit 2 to be tested, the strain gauge is mounted on a vertical support column 21 of the lifting unit and close to the connection part of the support head 22 and the vertical support column 21; three strain gauges form a strain rosette distributed at an angle of 45°, as shown in FIGS. 7,11 and 12, the strain rosette is mounted on an x-axis, a y-axis, and a u-axis at an angle of 45° with the x-axis, respectively, wherein, the x-axis is the lateral direction of the lifting unit and directed to the cantilever end 221 side of the support head 21, the y-axis is the longitudinal direction of the lifting unit and directed to the connection part, the u axis is positioned between the two; it can be seen that the strain gauge may be attached to the left and right sides of the vertical support column 21 (with respect to the front view of FIG. 1). The control unit comprises a collecting module capable of collecting pressure values of the three axes of the strain rosette, a calculation module capable of calculating the main stress value of the lifting unit to be tested according to the pressure values of the strain rosette, and a control module capable of outputting the main stress value in the calculation module; the collecting module is electrically connected to the calculation module, and the calculation module is electrically connected to the control module.

In the above, formulas for calculating the main stress value of the lifting unit to be tested by the calculation module are as follows:

$$\varepsilon_{max} = \frac{1}{2}\left[(\varepsilon_x + \varepsilon_y) + \sqrt{2[(\varepsilon_x - \varepsilon_u)^2 + (\varepsilon_u - \varepsilon_y)^2]}\right] \quad (1)$$

$$\varepsilon_{min} = \frac{1}{2}\left[(\varepsilon_x + \varepsilon_y) - \sqrt{2[(\varepsilon_x - \varepsilon_u)^2 + (\varepsilon_u - \varepsilon_y)^2]}\right] \quad (2)$$

$$tg2\alpha_0 = \frac{2\varepsilon_u - \varepsilon_x - \varepsilon_y}{\varepsilon_x - \varepsilon_y} \quad (3)$$

$$\sigma_1 = E \times (\varepsilon_{max} + \varepsilon_{min} \times v)/(1 - v^2) \quad (4)$$

$$\sigma_2 = E \times (\varepsilon_{min} + \varepsilon_{max} \times v)/(1 - v^2) \quad (5)$$

The calculation module sequentially calculates the main stress value according to the preset formulas, where E is an elasticity modulus, v is Poisson's ratio, ε is the strain in each direction of the strain rosette, $\varepsilon_{max}$ is the calculated maximum strain, $\varepsilon_{min}$ is the calculated minimum strain, $\alpha_0$ is an angle between the maximum main strain and the x-axis (as shown in FIG. 12), $\sigma_1$ is the main stress value consistent with the direction of $\varepsilon_{max}$ and $\sigma_2$ is the main stress value consistent with the direction of $\varepsilon_{min}$.

From the above formulas (1) (2) (3), the value and direction of the main strain are obtained, and then calculate the values of the main stresses σ1 and σ2 according to formulas (4) and (5), to provide a basis for judging the reliability of the structure. The above strain collection and stress calculation process may be completed automatically through a program setting in the control unit, with higher accuracy.

Suppose that n strain rosettes are provided, when an initial set pressure value is applied to the lifting unit to be tested, the strain rosette 1 to strain rosette n are connected in turn to record initial values respectively; when the pressure is continuously applied to a pressure value under multiplier of a preset rated load, the strain rosette 1 to strain rosette n connected in turn record and calculate n strain values of parts to be tested at this time, respectively.

Embodiment 4

A loading test test-and-control method of vehicle lifter lifting unit, uses any one of the loading test test-and-control system of vehicle lifter lifting unit above, and comprises the following steps specifically: the control unit sends a control signal to the loading unit according to an initial set pressure value; the hydraulic cylinder of the loading unit receives the control signal and applies the initial pressure to the lifting units to be tested (S1, S2, S3); during the process of loading pressure, the hydraulic cylinder continuously increases the pressure value to a pressure value under multiplier of a preset rated pressure value (S6, S7, S8), and during the process of loading pressure, the pressure sensor on the hydraulic cylinder feeds back pressure signals, applied by the hydraulic cylinder, to the control unit in real time (S8) to detect the loading pressure value; the control unit simultaneously adjusts the applied pressure value based on the feedback pressure to control the loading pressure (S6, S7).

The control and test of the lifting unit to be tested when loading the pressure are realized by the real-time sensing of the pressure sensor and the PID adjustment of the pressure of the hydraulic cylinder by the control unit.

At the same time, the test-and-control method of the present application may also test the deflection of the lifting unit to be tested, and a specific test method further comprises the following steps: when the hydraulic cylinder loads a pressure with the initial set pressure value, the displacement sensor senses an initial displacement value of the hydraulic cylinder and feeds back to the control unit, specifically a deflection detection unit in the control unit, and the displacement value then is recorded as A (S4); when the hydraulic cylinder applies the pressure to the pressure value under multiplier of the preset rated pressure value, the displacement sensor senses a second displacement value of the hydraulic cylinder and feeds back to the control unit (the deflection detection unit), and the displacement value then is recorded as B (S9); the control unit calculates the difference value between the second displacement value and the initial displacement value and outputs the difference value as the test of the deflection value of the lifting unit to be tested, that is, the value obtained by displacement value B minus displacement value A is just the deflection value of the lifting unit to be tested.

At the same time, the present application may test the stress of the lifting unit to be tested and further comprises the following steps: the control unit collects strain signals of the strain rosette attached on the lifting unit to be tested, the calculation module of the control unit calculates the main stress value according to the preset formulas to test the stress of the lifting unit to be tested.

In the step of testing the stress value, the preset formulas in the calculation module are as follows:

$$\varepsilon_{max} = \frac{1}{2}\left[(\varepsilon_x + \varepsilon_y) + \sqrt{2[(\varepsilon_x - \varepsilon_u)^2 + (\varepsilon_u - \varepsilon_y)^2]}\right], \quad (1)$$

$$\varepsilon_{min} = \frac{1}{2}\left[(\varepsilon_x + \varepsilon_y) - \sqrt{2[(\varepsilon_x - \varepsilon_u)^2 + (\varepsilon_u - \varepsilon_y)^2]}\right], \quad (2)$$

$$tg2\alpha_0 = \frac{2\varepsilon_u - \varepsilon_x - \varepsilon_y}{\varepsilon_x - \varepsilon_y}, \quad (3)$$

$$\sigma_1 = E \times (\varepsilon_{max} + \varepsilon_{min} \times v)/(1 - v^2), \quad (4)$$

$$\sigma_2 = E \times (\varepsilon_{min} + \varepsilon_{max} \times v)/(1 - v^2), \quad (5)$$

The calculation module sequentially calculates the main stress value according to the above preset formulas, where E is an elasticity modulus, v is Poisson's ratio, ε is the stress value in each direction of the strain rosette, and σ is the main stress value.

That is, the value and the direction of the main strain are obtained from the formulas (1) (2) (3), then the values of the main stress σ1 and σ2 are calculated by the formulas (4) (5) to provide a basis for judging the reliability of the lifting unit to be tested. The above strain collection and stress calculation processes are automatically completed by the control unit.

Specifically, when the system applies the pressure to be the initial set pressure value, a plurality of strain rosettes (for example, strain rosette 1 to strain rosette n) may be sequentially connected to a plurality of stress transmitters (stress detection units) provided in the control unit, to separately record the initial values (S5); when the system continuously applies the pressure to the pressure value under multiplier of the preset rated load, the strain rosette 1 to strain rosette n sequentially connected to a plurality of stress transmitters records and calculates strain values of n parts to be tested then (S10). The stress transmitter is cheap and may be reused, saving test cost.

In the above, the loading test test-and-control system and method of vehicle lifter lifting unit may be used for carrying out loading pressure control and test, the deflection test of a lifting column, and a stress test of main parts, thereby reducing the testing difficulty and testing cost and improving the testing precision.

Meanwhile, in the present application, the test-and-control system may also be provided with a touch screen, the control unit is connected to the touch screen. When it is needed to send a command to the test-and-control system, the touch screen may be operated to further control the transmission of a control signal of the control unit, through the touch screen; one may also intuitively see various pressure values, deflection values and the magnitude and change of stress, etc., which are more intuitive.

Embodiment 5

Figure 13:
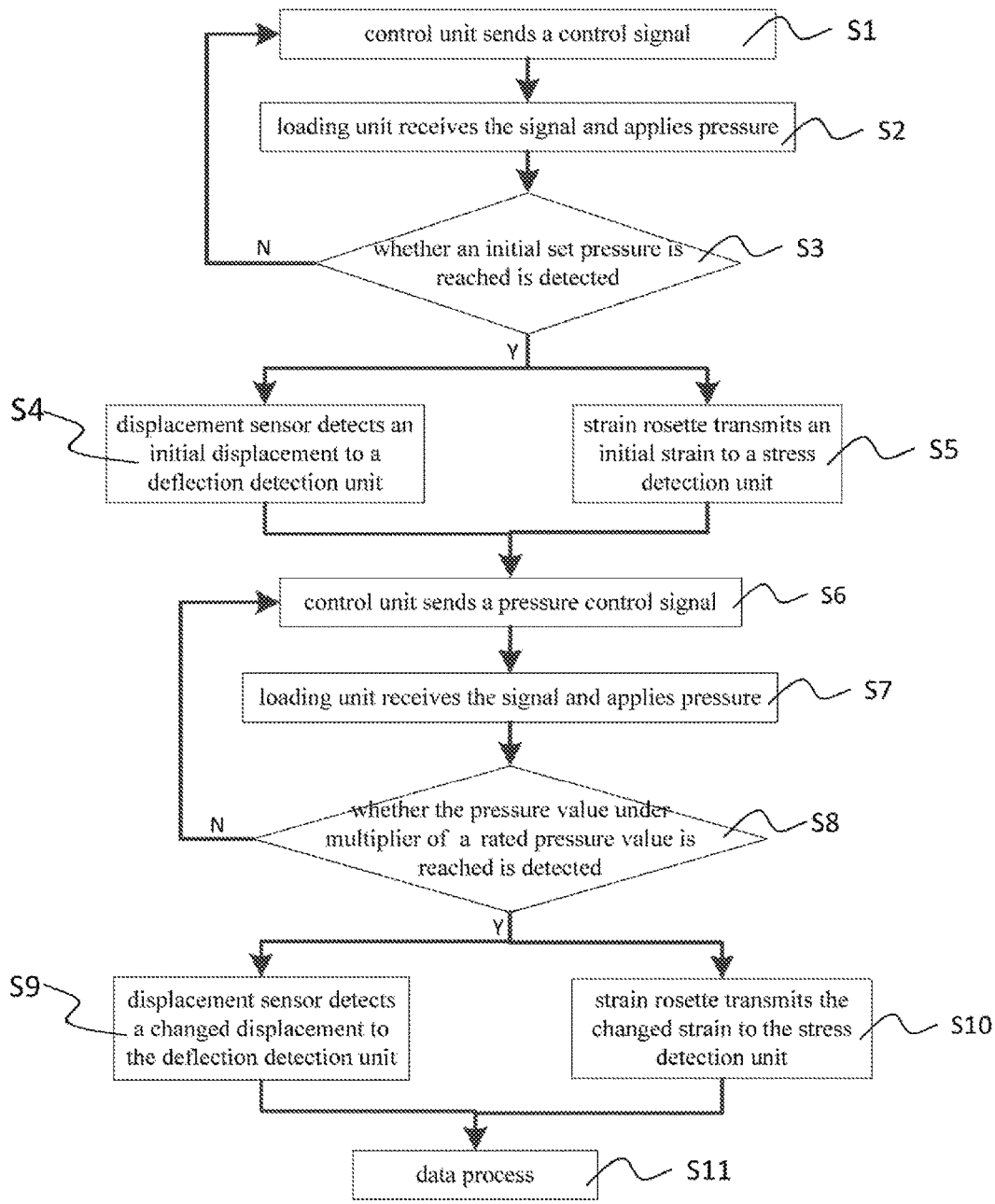
FIG. 13 is a flow chart of a test-and-control method.

This embodiment is used as an additional description of Embodiment 4, and specifically, refers to FIG. 13, a loading test test-and-control method of vehicle lifter lifting unit specifically comprises the following steps:

S1: the control unit sends the pressure control signal to the loading unit;

S2: the loading unit receives the control signal, and the hydraulic cylinder of the loading unit applies pressure to the lifting unit to be tested;

S3: whether the applied pressure reaches the initial set pressure value is detected; if not reached, return back to S1; if reached, go to a nest step; this step may be realized by the pressure sensor feeding back pressure signals, applied by the hydraulic cylinder, to the control unit in real time;

wherein steps S1-S3 are set to reach the initial set pressure value; If the pressure value given at the beginning is the initial set pressure value, the feedback step may be simplified accordingly;

S4: the displacement sensor detects the initial displacement and feeds back to the deflection detection unit (positioned in the control unit);

S5: the strain rosette transmits the initial strain to the stress detection unit (positioned in the control unit);

Wherein S4 and S5 may be selected as parallel steps according to specific settings of the device.

S6: the control unit sends a pressure control signal to the loading unit;

S7: the loading unit receives the control signal, and the hydraulic cylinder of the loading unit applies pressure to the lifting unit to be tested;

S8: whether the applied pressure reaches the pressure value under multiplier of the rated pressure value is detected; if not reached, return back to S6; if reached, go to a next step; this step may also be realized by the pressure sensor feeding back pressure signals, applied by the hydraulic cylinder, to the control unit in real time;

S9: the displacement sensor detects the changed displacement and feeds back to the deflection detection unit (positioned in the control unit);

S10: the strain rosette transmits the changed strain to stress detection unit (located in control unit);

Wherein steps S9 and S10 correspond to steps S4 and S5; that is, there is no S9 without S4, and there is no S10 without S5; S9 and S10 may also be in parallel relationship;

S11: the collected pressure, deflection and strain data are processed.

What is claimed is:

1. A loading test test-and-control system of vehicle lifter lifting unit, comprising a base, wherein,
   the base is provided thereon with a support bracket;
   the support bracket is provided with a loading unit for applying a loading force to a lifting unit to be tested;
   the loading unit is electrically connected with a control unit which controls a pressure applied by the loading unit according to a set value;
   the lifting unit to be tested is directly mounted on the base; and the lifting unit to be tested comprises a support head and a vertical support column;
   the support bracket comprises a first support column and a second support column, both of which are provided on the base; a horizontal beam is provided between the first support column and the second support column; the lifting unit to be tested is positioned between the first support column and the second support column, and is positioned below the horizontal beam; the loading unit is mounted on the horizontal beam and positioned between the horizontal beam and the lifting unit to be tested;
   the loading unit comprises a hydraulic cylinder, a fixed end of the hydraulic cylinder is mounted on the support bracket and below the horizontal beam, a piston end of the hydraulic cylinder and a joint provided at a lower end of the piston end are at a side close to the lifting unit to be tested; a bottom of the piston end of the hydraulic cylinder is provided with a pressure sensor capable of detecting loading pressure of the hydraulic cylinder, the pressure sensor is positioned below the joint, and the pressure sensor is connected to the control unit to transmit a pressure signal sensed by the pressure sensor to the control unit; the joint and the pressure sensor are movably connected via a connecting member.

2. The test-and-control system according to claim 1, wherein, the connecting member comprises a first connecting member and a second connecting member; wherein, an upper end of the first connecting member is fixed on a bottom of the piston end or on the joint, a lower end of the second connecting member is mounted on the pressure sensor; the first connecting member is provided with a first hole, and the second connecting member is provided thereon with a second hole matching the first hole; the first connecting member and the second connecting member are mounted together by providing a fixing member in the first hole and the second hole; wherein at least one of the first hole or the second hole is a vertically long hole.

3. The test-and-control system according to claim 2, wherein, a lower end of the pressure sensor is provided with a sensor end cap; and the lower end of the second connecting member is mounted on the sensor end cap.

4. The test-and-control system according to claim 1, wherein, the hydraulic cylinder is equipped with a displacement sensor, used for detecting a displacement signal of the hydraulic cylinder.

5. The test-and-control system according to claim 4, wherein, an upper end of the displacement sensor is mounted on the fixed end, and a lower end thereof is mounted on the bottom of the piston end or on the joint; the control unit further comprises a displacement collecting module capable of collecting a displacement signal and a displacement output module capable of outputting a displacement signal value, and the modules are electrically connected with the control unit.

6. The test-and-control system according to claim 1, wherein, the control unit is electrically connected with strain gauges attached to the lifting unit to be tested, the strain gauges form a three-dimensional strain rosette with 45° angle distribution; the control unit comprises a collecting module capable of collecting three-dimensional stress values of the strain rosette, a calculation module capable of calculating a main stress value of the lifting unit to be tested according to the stress values of the strain rosette, and a control module capable of outputting the main stress value in the calculation module; the collecting module is electrically connected to the calculation module, and the calculation module is electrically connected to the control module.

7. The test-and-control system according to claim 6, wherein, the strain gauge is provided on the vertical support column of the lifting unit to be tested and close to a connection part of the vertical support column and the support head; three strain gauges form one strain rosette, the strain rosette comprises a first strain gauge provided horizontally, a second strain gauge provided vertically and a third strain gauge positioned between the horizontal direction and the vertical direction; wherein an x-axis where the first strain gauge is positioned is directed to the cantilever end of the support head, a y-axis where the second strain gauge is positioned is directed to the connecting direction of the support head and the vertical support column, a u-axis where the third strain gauge is positioned is positioned between the x-axis and the y-axis.

8. The test-and-control system according to claim 4, wherein, the control unit is electrically connected with strain gauges attached to the lifting unit to be tested, the strain gauges form a three-dimensional strain rosette with 45° angle distribution; the control unit comprises a collecting module capable of collecting three-dimensional stress values of the strain rosette, a calculation module capable of calculating a main stress value of the lifting unit to be tested according to the stress values of the strain rosette, and a control module capable of outputting the main stress value in the calculation module; the collecting module is electrically connected to the calculation module, and the calculation module is electrically connected to the control module.

9. The test-and-control system according to claim 8, wherein, the strain gauge is provided on the vertical support column of the lifting unit to be tested and close to a connection part of the vertical support column and the support head; three strain gauges form one strain rosette, the strain rosette comprises a first strain gauge provided horizontally, a second strain gauge provided vertically and a third strain gauge positioned between the horizontal direction and the vertical direction; wherein an x-axis where the first strain gauge is positioned is directed to the cantilever end of the support head, a y-axis where the second strain gauge is positioned is directed to the connecting direction of the support head and the vertical support column, a u-axis where the third strain gauge is positioned is positioned between the x-axis and the y-axis.

10. A loading test test-and-control system of vehicle lifter lifting unit, comprising a base, wherein,
the base is provided thereon with a support bracket capable of installing a lifting unit to be tested;
the support bracket is provided with a loading unit for applying a loading force to the lifting unit to be tested;
the loading unit is electrically connected with a control unit which controls a pressure applied by the loading unit according to a set value;
the support bracket comprises a first support column and a second support column, both of which are provided on the base; a horizontal beam is provided between the first support column and the second support column; the lifting unit to be tested is positioned between the first support column and the second support column, and is positioned below the horizontal beam; the loading unit is mounted on the horizontal beam and positioned between the horizontal beam and the lifting unit to be tested;
the loading unit comprises a hydraulic cylinder, a fixed end of the hydraulic cylinder is mounted on the support bracket and below the horizontal beam, a piston end of the hydraulic cylinder and a joint provided at a lower end of the piston end are at a side close to the lifting unit to be tested; a bottom of the piston end of the hydraulic cylinder is provided with a pressure sensor capable of detecting loading pressure of the hydraulic cylinder, the pressure sensor is positioned below the joint, and the pressure sensor is connected to the control unit to transmit a pressure signal sensed by the pressure sensor to the control unit; the joint and the pressure sensor are movably connected via a connecting member.

11. The test-and-control system according to claim 10, wherein,
the connecting member comprises a first connecting member and a second connecting member; wherein, an upper end of the first connecting member is fixed on a bottom of the piston end or on the joint, a lower end of the second connecting member is mounted on the pressure sensor; the first connecting member is provided with a first hole, and the second connecting member is provided thereon with a second hole matching the first hole; the first connecting member and the second connecting member are mounted together by providing a fixing member in the first hole and the second hole; wherein at least one of the first hole or the second hole is a vertically long hole;
a lower end of the pressure sensor is provided with a sensor end cap; and the lower end of the second connecting member is mounted on the sensor end cap.

12. The test-and-control system according to claim 10, wherein, the hydraulic cylinder is equipped with a displacement sensor, used for detecting a displacement signal of the hydraulic cylinder;
an upper end of the displacement sensor is mounted on the fixed end, and a lower end thereof is mounted on the bottom of the piston end or on the joint; the control unit further comprises a displacement collecting module capable of collecting a displacement signal and a displacement output module capable of outputting a displacement signal value, and the modules are electrically connected with the control unit.

13. The test-and-control system according to claim 12, wherein, the control unit is electrically connected with strain gauges attached to the lifting unit to be tested, the strain gauges form a three-dimensional strain rosette with 45° angle distribution; the control unit comprises a collecting module capable of collecting three-dimensional stress values of the strain rosette, a calculation module capable of calculating a main stress value of the lifting unit to be tested according to the stress values of the strain rosette, and a control module capable of outputting the main stress value in the calculation module; the collecting module is electrically connected to the calculation module, and the calculation module is electrically connected to the control module.

14. A loading test test-and-control method of vehicle lifter lifting unit, using a loading test test-and-control system, the loading test test-and-control system comprising a base, wherein, the base is provided thereon with a support bracket;
the support bracket is provided with a loading unit for applying a loading force to a lifting unit to be tested;
the loading unit is electrically connected with a control unit which controls a pressure applied by the loading unit according to a set value;
the lifting unit to be tested is directly mounted on the base; and the lifting unit to be tested comprises a support head and a vertical support column;
the loading unit comprises a hydraulic cylinder, a fixed end of the hydraulic cylinder is mounted on the support bracket, a piston end is close to the lifting unit to be tested; a bottom of the piston end of the hydraulic cylinder is provided with a pressure sensor capable of detecting loading pressure of the hydraulic cylinder, and the pressure sensor is connected to the control unit to transmit a pressure signal sensed by the pressure sensor to the control unit; the hydraulic cylinder is further equipped with a displacement sensor, the displacement sensor is used for detecting a displacement signal of the hydraulic cylinder; and
the method comprising the following steps:
the control unit sends a control signal to the loading unit according to an initial set pressure value;
the hydraulic cylinder of the loading unit receives the control signal and applies the initial set pressure value as an initial pressure to the lifting unit to be tested;
the hydraulic cylinder continuously increases the pressure value to a pressure value under multiplier of a preset rated pressure value during the process of pressure loading, and
the pressure sensor connected with the hydraulic cylinder feeds back pressure signals in real-time, applied by the hydraulic cylinder, to the control unit to detect the load pressure value;
the control unit simultaneously adjusts the applied pressure value according to the feedback pressure to control the loading pressure;
when the hydraulic cylinder loads the pressure at the initial set pressure value, the displacement sensor senses an initial displacement value of the hydraulic cylinder and feeds back to the control unit and when the hydraulic cylinder applies the pressure to be the pressure value under multiplier of the preset rated pressure value, the displacement sensor senses a second displacement value of the hydraulic cylinder and feeds back to the control unit the control unit calculates a difference value between the second displacement value and the initial displacement value and outputs the difference value as a test of a deflection value of the lifting unit to be tested.

15. The test-and-control method according to claim 14, further comprising the following steps: the control unit collects stress signals of the strain rosette attached on the lifting unit to be tested; the calculation module of the control unit calculates the main stress values according to preset formulas to test the stress of the lifting unit to be tested.

16. The test-and-control method according to claim 15, wherein, in the step of testing the stress value, the preset formulas in the calculation module are as follows:

$$\varepsilon_{max} = \frac{1}{2}\left[(\varepsilon_x + \varepsilon_y) + \sqrt{2[(\varepsilon_x - \varepsilon_u)^2 + (\varepsilon_u - \varepsilon_y)^2]}\,\right], \quad (1)$$

$$\varepsilon_{min} = \frac{1}{2}\left[(\varepsilon_x + \varepsilon_y) = \sqrt{2[(\varepsilon_x - \varepsilon_u)^2 + (\varepsilon_u - \varepsilon_y)^2]}\,\right], \quad (2)$$

$$tg2\alpha_0 = \frac{2\varepsilon_u - \varepsilon_x - \varepsilon_y}{\varepsilon_x - \varepsilon_y}, \quad (3)$$

$$\sigma_1 = E \times (\varepsilon_{max} + \varepsilon_{min} \times v)/(1 - v^2), \quad (4)$$

$$\sigma_2 = E \times (\varepsilon_{min} + \varepsilon_{max} \times v)/(1 - v^2); \quad (5)$$

the calculation module sequentially calculates the stress values according to the preset formulas; where, E is an elasticity modulus, $v$ is Poisson's ratio, $\varepsilon$ is the strain in each direction of the strain rosette, $\sigma$ is the main stress value.

17. The test-and-control system according to claim 3, wherein, the hydraulic cylinder is equipped with a displacement sensor, used for detecting a displacement signal of the hydraulic cylinder.

18. The test-and-control system according to claim 17, wherein, an upper end of the displacement sensor is mounted on the fixed end, and a lower end thereof is mounted on the bottom of the piston end or on the joint; the control unit further comprises a displacement collecting module capable of collecting a displacement signal and a displacement output module capable of outputting a displacement signal value, and the modules are electrically connected with the control unit.

19. A loading test test-and-control system of vehicle lifter lifting unit, comprising a base, wherein, the base is provided thereon with a support bracket capable of installing a lifting unit to be tested;
the support bracket is provided with a loading unit for applying a loading force to the lifting unit to be tested;
the loading unit is electrically connected with a control unit which controls a pressure applied by the loading unit according to a set value;
the loading unit comprises a hydraulic cylinder, a fixed end of the hydraulic cylinder is mounted on the support bracket, a piston end is close to the lifting unit to be tested; a bottom of the piston end of the hydraulic cylinder is provided with a pressure sensor capable of detecting loading pressure of the hydraulic cylinder, and the pressure sensor is connected to the control unit to transmit a pressure signal sensed by the pressure sensor to the control unit;
the hydraulic cylinder is equipped with a displacement sensor, used for detecting a displacement signal of the hydraulic cylinder;
an upper end of the displacement sensor is mounted on the fixed end, and a lower end thereof is mounted on the bottom of the piston end or on a joint provided at a lower end of the piston end; the control unit further comprises a displacement collecting module capable of collecting a displacement signal and a displacement output module capable of outputting a displacement signal value, and the modules are electrically connected with the control unit.

* * * * *